(12) United States Patent
Miesak et al.

(10) Patent No.: US 8,437,517 B2
(45) Date of Patent: May 7, 2013

(54) LATENT FINGERPRINT DETECTORS AND FINGERPRINT SCANNERS THEREFROM

(75) Inventors: Edward Miesak, Windermere, FL (US); V. Edward Gold, Jr., Orlando, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 282 days.

(21) Appl. No.: 13/049,351

(22) Filed: Mar. 16, 2011

(65) Prior Publication Data

US 2012/0105586 A1    May 3, 2012

Related U.S. Application Data

(60) Provisional application No. 61/409,753, filed on Nov. 3, 2010.

(51) Int. Cl.
*G06K 9/00* (2006.01)
(52) U.S. Cl.
USPC .............................. 382/124; 382/116; 348/61
(58) Field of Classification Search .......................... None
See application file for complete search history.

(56) References Cited

U.S. PATENT DOCUMENTS

| | | | | |
|---|---|---|---|---|
| 4,120,585 A | * | 10/1978 | DePalma et al. | 356/71 |
| 4,783,167 A | * | 11/1988 | Schiller et al. | 356/71 |
| 4,785,171 A | * | 11/1988 | Dowling et al. | 250/227.28 |
| 5,109,427 A | * | 4/1992 | Yang | 382/127 |
| 5,210,588 A | * | 5/1993 | Lee | 356/71 |
| 5,233,404 A | * | 8/1993 | Lougheed et al. | 356/71 |
| 5,313,265 A | | 5/1994 | Hayes et al. | |
| 5,812,252 A | * | 9/1998 | Bowker et al. | 356/71 |
| 5,963,657 A | * | 10/1999 | Bowker et al. | 382/127 |
| 6,115,484 A | * | 9/2000 | Bowker et al. | 382/127 |
| 6,643,390 B1 | * | 11/2003 | Clark et al. | 382/124 |
| 6,665,427 B1 | * | 12/2003 | Keagy et al. | 382/124 |
| 6,668,071 B1 | * | 12/2003 | Minkin et al. | 382/124 |

(Continued)

FOREIGN PATENT DOCUMENTS

| | | |
|---|---|---|
| CN | 2603449 | 2/2004 |
| CN | 201210214 | 3/2009 |
| JP | 06-147852 A | 5/1994 |
| JP | 2001-034738 A | 2/2001 |

OTHER PUBLICATIONS

International Search Report and Written Opinion of the International Searching Authority for corresponding Application No. PCT/US2011/059008 dated May 29, 2012.

*Primary Examiner* — Manav Seth
(74) *Attorney, Agent, or Firm* — Beusse Wolter Sanks Mora & Maire, P.A.

(57) ABSTRACT

An automatic fingerprint system includes an optical sensor having a first light source that provides a collimated beam for interrogating a first sample surface, and a camera including a lens and a photodetector array having a camera field of view ($FOV_{CAMERA}$) large enough to image the first sample surface. The camera is critical angle positioned relative to the first light source to receive specular reflection (glare) from the first sample surface to generate image data from the glare. The first light source and camera have substantially equal and opposite numerical apertures (NAs). A computer or processor that includes reference fingerprint templates receives a digitized form of the image data, and includes data processing software for (i) comparing the image data to reference fingerprint templates to determine whether the image data includes at least one fingerprint and (ii) for generating a fingerprint image if the fingerprint is determined to be present.

24 Claims, 8 Drawing Sheets

U.S. PATENT DOCUMENTS

| | | | |
|---|---|---|---|
| 7,181,052 B2* | 2/2007 | Fujieda | 382/124 |
| 7,212,330 B2* | 5/2007 | Seo et al. | 359/298 |
| 7,346,200 B1* | 3/2008 | Tsipouras et al. | 382/128 |
| 7,489,391 B2 | 2/2009 | Engheta et al. | |
| 7,787,110 B2* | 8/2010 | Raguin et al. | 356/71 |
| 2003/0118219 A1* | 6/2003 | Higuchi et al. | 382/125 |
| 2005/0141756 A1 | 6/2005 | Lee et al. | |
| 2007/0280513 A1 | 12/2007 | Engheta et al. | |

* cited by examiner

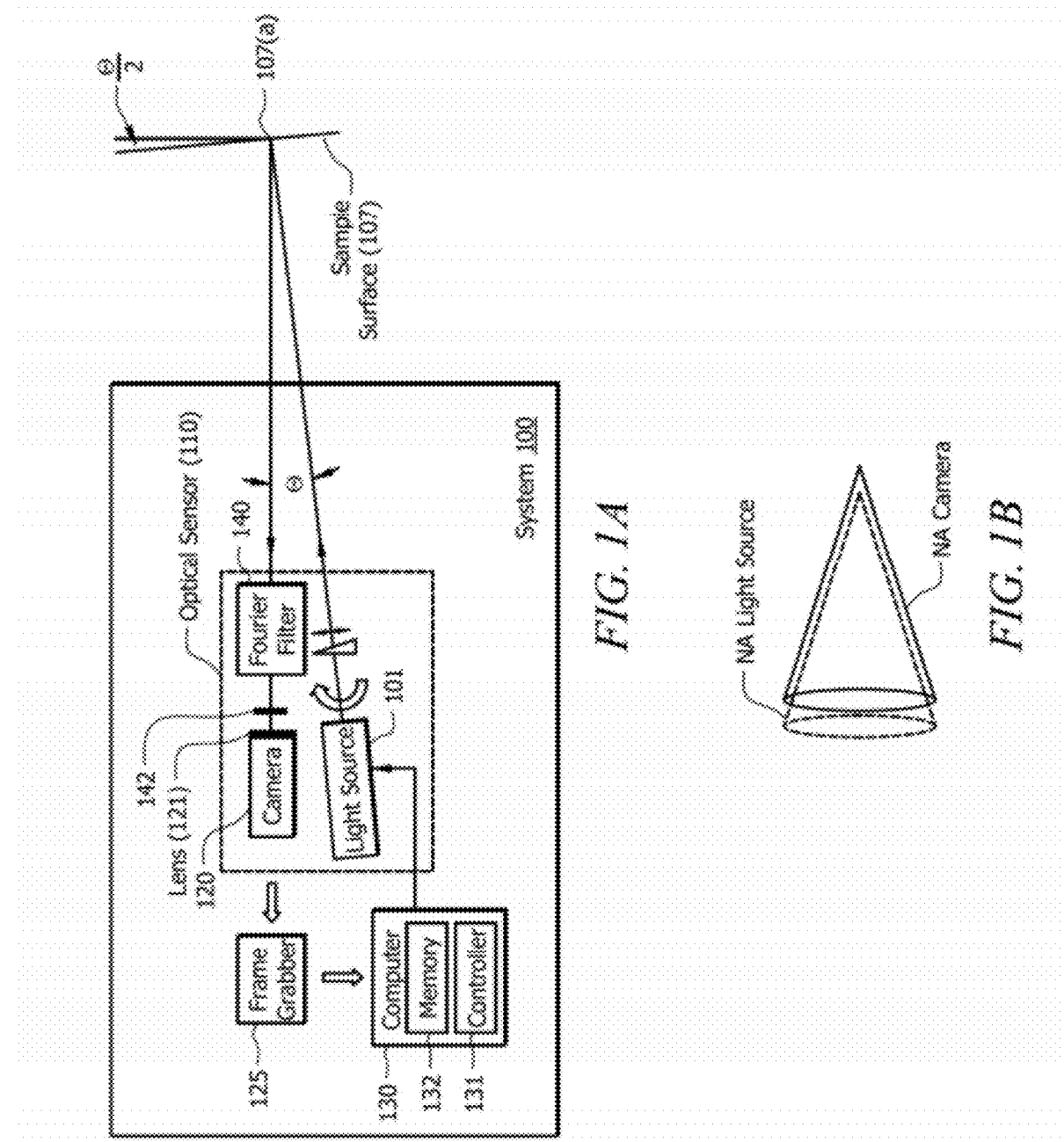

LATENT FINGERPRINT DETECTORS AND FINGERPRINT SCANNERS THEREFROM

CROSS REFERENCE TO RELATED APPLICATIONS

This application claims the benefit of Provisional Application Ser. No. 61/409,753 entitled "IMAGING OF OPTICAL GLARE TO ENHANCE OBJECT FEATURES IN IMAGES", filed Nov. 3, 2010, which is herein incorporated by reference in its entirety.

U.S. GOVERNMENT RIGHTS

The U.S. Government has certain rights to disclosed embodiments based on Contract No. W911NF-10-C-0029 between Lockheed Martin Corporation and the U.S. Army.

FIELD

Disclosed embodiments relate to non-contact automatic optical detection of latent fingerprints.

BACKGROUND

Latent prints are invisible fingerprint impressions left on solid surfaces following surface contact caused by the perspiration on the ridges of an individual's skin on their fingers coming in contact with a surface and leaving perspiration behind, making an invisible impression on it. Perspiration is known to contain water, salt, amino acids, and oils, which allows impressions to be made. The natural oils of the body preserve the fingerprint, which is utterly distinct so that no two humans have the same fingerprints.

Conventional methods for extracting fingerprints usually involve adding chemicals or powders to the print. Such conventional methods can present an immediate dilemma in that they force the investigator to make a decision as to whether to dust for prints versus swabbing for DNA evidence.

Automatic non-contact latent fingerprint detection systems are also known that avoid the need to add chemicals or powders that can disturb the surface chemicals of the fingerprint. Such systems generally include a single light source, utilize only diffuse reflectance (reject specular reflection (glare)), and are generally limited to fingerprinting the area of one's finger, or an area about that size.

SUMMARY

Disclosed embodiments include non-contact automatic optical fingerprint systems that include a critically aligned optical sensor comprising a light source critical angle positioned relative to a camera to utilize specular reflection from an irradiated sample surface. In contrast, conventional optical fingerprint systems reject specular reflection (glare) and process only diffuse reflection. It has been discovered that fingerprint features can be seen in images enabled by processing glare that cannot be seen in images generated using conventional diffuse reflected light. When the optical sensor is critical angle positioned and the camera exposure time and gain settings are set so that the specular reflections received do not saturate the camera's photosensor array, the diffuse reflections from interrogated sample surfaces will appear (relatively) very dim. In this arrangement, the diffuse reflections may not be visible at all. The critically aligned optical sensor and camera settings can therefore act as a filter discriminating highly against diffuse reflections from scattering surfaces therefore providing a "geometric filter" that essentially only accepts glare (i.e., ≧98% of the photons processed by the camera are from the glare).

Discrimination for glare can be further enhanced when the numerical aperture (NA) of the lens is =0 so that $NA_{CAMERA}=0$. As known in optics, the NA of an optical system is a dimensionless number that characterizes the range of angles over which an optical system can accept light (for a light collector, e.g., camera) or emit light (for a light source). Disclosed embodiments also recognize that having the light source and the camera have equal and opposite NAs that are aligned together provides even more highly discriminating results for glare. As used herein, the light source and the camera having "substantially equal and opposite NAs" refers to the respective NAs being within 10%, and typically within 5%, of a magnitude of one another, and being opposite in sign. Disclosed fingerprint systems comprise a critically aligned optical sensor that includes a first light source for interrogating a first sample surface within a region of interest with a collimated beam that can provide collimated photons that uniformly extend over the first sample surface. As used herein, "uniformly extended" refers to an irradiated intensity of the collimated beam that varies ≧±20% across the area of the first sample surface. The camera comprises a lens and a photodetector array optically coupled to the lens that has a camera field of view ($FOV_{CAMERA}$), wherein the $FOV_{CAMERA}$ is sufficiently large to image at least substantially an entire area of the first sample surface.

A computer or processor having associated memory that includes reference fingerprint templates is coupled to receive a digitized form of the image data from the camera. The computer or processor includes data processing software for (i) comparing the digitized form of the image data to the reference fingerprint templates to determine whether the image data includes at least one fingerprint, and (ii) for generating a fingerprint image if a fingerprint is determined to be present.

Automatic fingerprint scanning systems are also disclosed. Disclosed automatic fingerprint scanning systems comprise a disclosed automatic optical fingerprint system together with a scanner mechanically coupled to the optical sensor for scanning the optical sensor across a plurality of different surface portions within the region of interest, and optionally also a wireless transmitter for transmitting data representing fingerprints detected by the system to at least one remote site.

BRIEF DESCRIPTION OF THE DRAWINGS

FIG. 1A is a depiction of an example fingerprint system comprising a critically aligned optical sensor including a camera and a light source, where the light source provides a uniformly extended collimated beam for interrogating sample surfaces including a first sample surface within a region of interest, and a computer or processor for data processing the glare received by the camera, according to an example embodiment.

FIG. 1B illustrates a depiction of NA matching along with NA alignment between a light source and a camera for the case of cone-shaped emission and collection NAs, according to an example embodiment.

DETAILED DESCRIPTION

Figure 1C:
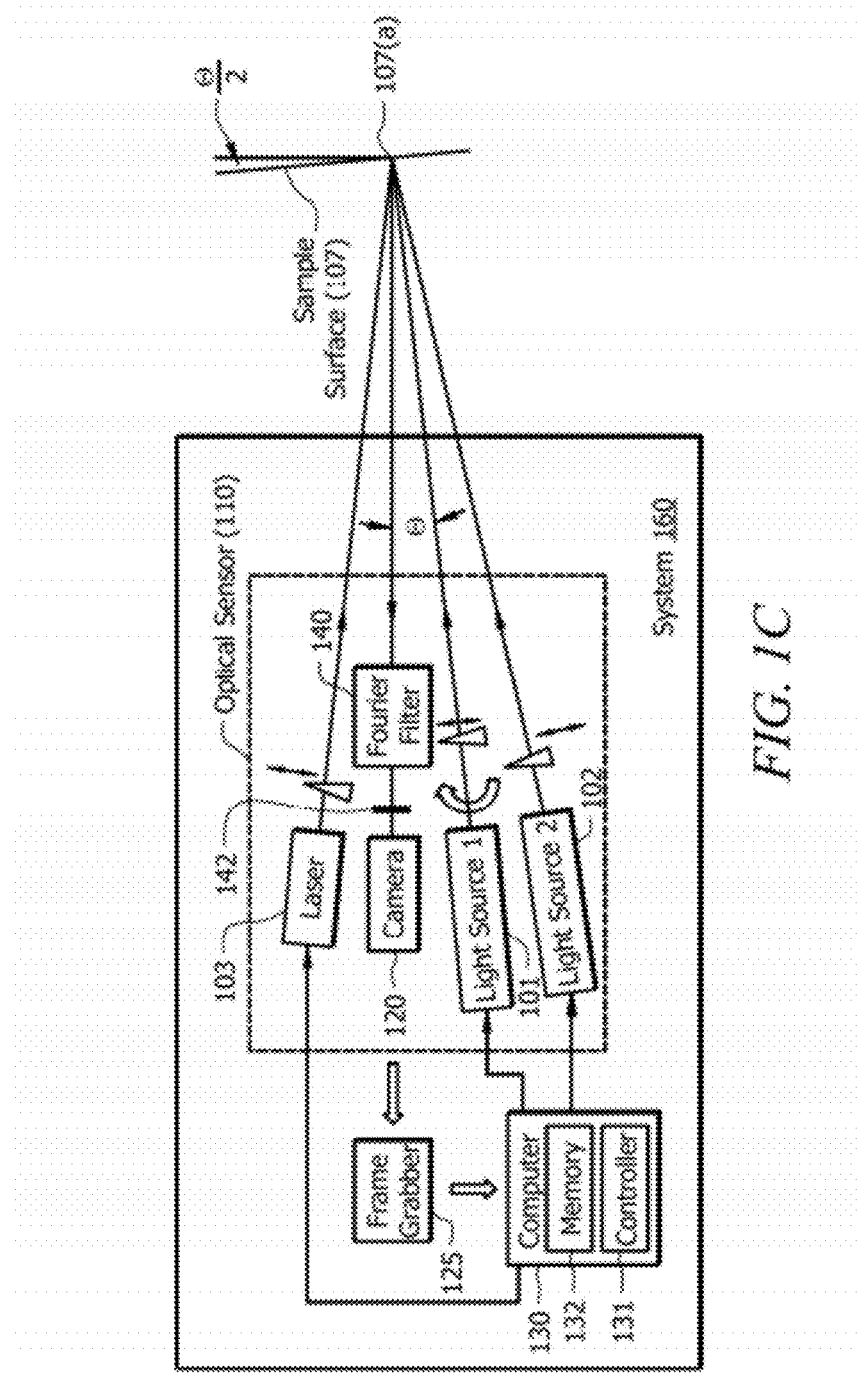
FIG. 1C is a depiction of an example fingerprint system comprising a critically aligned optical sensor including a camera and a light source, where the light source provides a uniformly extended collimated beam for interrogating sample surfaces including a first sample surface within a region of interest, along with other non-critically aligned light sources, and a computer or processor for data processing the glare received by the camera, according to an example embodiment.

Disclosed embodiments are described with reference to the attached figures, wherein like reference numerals, are used throughout the figures to designate similar or equivalent elements. The figures are not drawn to scale and they are provided merely to illustrate aspects disclosed herein. Several disclosed aspects are described below with reference to example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. Disclosed embodiments are not limited by the illustrated ordering of acts or events, as some acts may occur in different orders and/or concurrently with other acts or events. Furthermore, not all illustrated acts or events are required to implement a methodology in accordance with this Disclosure.

Disclosed embodiments recognize reflections from a sample surface includes two distinct kinds of reflection, specular reflection (glare) and diffuse reflection, and disclosed embodiments utilize at least the specular reflection component to optically obtain fingerprints from the sample surface. As known in the art, for specular reflection imaging the angles of incidence and reflection are set equal, while for the diffuse reflection case the reflected intensity may approximately have an effectively uniform distribution over all directions in a hemisphere. Most surfaces exhibit both types of reflection. Disclosed embodiments are in contrast to conventional optical imaging systems including conventional fingerprint systems that are configured to reject specular reflection and process only diffuse reflection.

FIG. 1A is a depiction of an example fingerprint system 100 comprising a critically aligned optical sensor 110 including a camera 120 comprising a lens 121 and a light source 101, where the light source 101 provides a uniformly extended collimated beam for interrogating sample surfaces 107 including a first sample surface 107(a) within a region of interest, and a computer or processor 130 for data processing the glare received by the camera 120, according to an example embodiment. The collimated beam provided by light source 101 has a spatial extent $\geq FOV_{CAMERA}$. In one specific embodiment the interrogation area provided by the collimated beam is 50 μm×50 μm, and the $FOV_{CAMERA}$ is $\leq$50 μm×50 μm.

As depicted in FIG. 1B, the light source 101 and the camera 120 can have substantially equal and opposite NAs that are aligned together to provide highly discriminating results for specular reflection. One method for NA alignment is to use the apparatus itself with a good sample and a set of neutral density optical filters. Adjustment can be made using bright light until the best response is obtained. A filter can be added to dim the illuminating light and the best performance can be obtained again. Another filter is then added, etc. For instance, if the two NAs are conically shaped and opposite in sign they can be stacked almost perfectly one on top of the other as shown in FIG. 1B.

Optically aligning the light source which provides a uniformly extended collimated beam over the sample surface and camera NAs then uniformly filling the camera NA makes the glare field uniform across the full $FOV_{CAMERA}$. The Inventor has recognized that use of a uniform glare field maximizes the dynamic range of the imaging system, since non-uniformities in the illumination field serve as a noise floor. A wide dynamic range with good SNR desirably provides high contrast.

The light source 101 can comprise a broadband light source. For example, the broadband light source can comprise a fluorescent light source, such as a plurality of parallel aligned (i.e., stacked) fluorescent tubes. In another embodiment the collimated beam provided by light source 101 comprises a narrowband beam defined herein as <1 nm Full Width Half Max (FWHM).

A narrowband beam can be realized by a narrowband light source (e.g., laser), or a broadband light source (see below) and a spectrometer. In some embodiments the collimated beam is at one or more UV wavelengths or one or more LWIR wavelengths that each correspond to significantly enhanced absorption for fingerprint oil, defined herein to be present at wavelengths where absorption increases by at least 6.5% as compared to the absorption in a conventional range from visible light range to 3 μm. Increased absorption has been found to provide an improvement in contrast vs. the sample surface that provides the background in the image. See FIG. 4 described below that evidences some UV and IR wavelengths that provide significantly enhanced absorption. In one embodiment the UV wavelength is between 100 and 300 nm, and the LWIR wavelength can be at 3.42 µm, 5.71 µm, 6.9 µm, or 8.8 µm, which all represent significantly enhanced absorption wavelengths for fingerprint oil.

Light source 101 can provide either non-polarized or polarized light. Polarized light may be of advantage when the sample surface 107 is held at an extreme angle, something analogous to Brewster's angle (polarization angle). This angle is defined by the surface material and surface roughness/texture.

Camera 120 comprises lens 121. Camera 120 can comprise a variety of different camera types, such a commercial off-the shelf (COTS) CCD/CMOS digital camera. The lens magnification, camera sensor size, and pixel count can be designed to produce a minimum resolution that is compatible with existing requirements. For example, 500 DPI is the current FBI standard.

In one embodiment, the camera 120 is sensitive to radiation including UV radiation in the range from about 100 nm to 300 nm. This UV imaging capability can be provided by adding a layer of UV sensitizer material to the sensor associated with the camera 120. One such material has the commercial name Lumigen (Lumigen, Inc. (a Beckman Coulter Company Southfield, Mich.). This layer absorbs UV light and up converts it to a wavelength that photodetectors such as CCD photodetectors can efficiently detect.

In one embodiment the lens 121 is selected to provide $NA_{CAMERA}=0$. For example, a double telecentric lens can provide $NA_{CAMERA}=0$ which results in the $FOV_{CAMERA}=area$ of the lens 121. The camera 120 is coupled to a computer or processor 130 via a frame grabber 125. As known in the art, a frame grabber 125 is an electronic device that captures individual, digital still frames from an analog video signal or a digital video stream. A computer or processor 130 includes a controller 131 that can dynamically control the intensity of light provided by light source 101, and at least one memory 132. The intensity of light source 101 can be set to approach but not reach saturation of the photodetectors in camera 120.

The standoff distance during imaging operations is generally set by the optics of the camera 120. A typical standoff distance between the optical sensor 110 and sample surface 107 is about 12 inches, but can be at other distances, such as 4 to 20 inches, for example.

Light source 101 can be dynamically angle tuned to maintain critical angle alignment shown as at an angle e with respect to the camera 120. For example, a movable laser illuminated mirror can be used to adjust the critical angle lighting condition to produce the best results. In one embodiment both the light source 101 and the camera 120 are secured to a fixture to ensure maintaining critical angle alignment.

System 100 includes at least one detection filter, shown in FIG. 1 as Fourier filter 140 and a Rugate notch filter 142. Notch filter 142 is included for embodiments including a laser (not shown), such as for critical alignment purposes, or as a diffuse scatter light source. Fourier filter 140 functions to match fingerprint features as well as suppress background features, such as grains in the paper in the case of a paper sample surface, such as for Raman imaging.

Disclosed embodiments recognize in order to detect fingerprints that may be on a wide variety of different surfaces, such as tools (e.g., wrenches), guns, phones/PDAs and CD cases, multiple different light sources may be helpful. Each light source can provides a different kind of light, such as white light and narrowband light, such as in the UV or IR. Thus light from each light source will scatter off the interrogated sample surface differently. The light sources are generally used one at a time, with each of the light sources producing a different effect on the latent fingerprint. There is a high probability that every latent fingerprint on a given sample surface will respond to one or more of these light sources and become visible to the camera 120 recording the results.

FIG. 1C is a depiction of an example fingerprint system 160 comprising a critically aligned optical sensor including a camera and a light source 101, where the light source 101 provides a uniformly extended collimated beam for interrogating sample surfaces including a first sample surface within a region of interest, along with other non-critically aligned light sources 102 and 103, according to an example embodiment. Diffuse scatter from non-critically aligned light sources 102 and 103 allows the background to be characterized so that the background can be subtracted out from the image data, such as text on paper in the case of certain paper-based samples.

System 160 includes a computer or processor 130 for data processing the glare and diffuse refection data received by the camera 120. In one embodiment light source 102 provides non-critical angled incandescent light, and light source 103 comprising a non-critical aligned laser. Light sources 101-103 each can include dynamic intensity adjustment. In typical system operation, the respective light sources 101-103 individually illuminate the sample surface 107 for separate interrogations.

Light from laser 103 can reveal latent fingerprints that the other two light sources 101 and 102 cannot. The laser 103 is used to excite the sample surface in a very specific (narrow) spectral band and time domain, such as at 532 nm. Spectral/temporal filtering methods can be used to extract the desired information from the laser illumination of the sample surface. The type of camera used to record the results depends on the type of optical filtering required to extract the data. For instance, if Raman imaging is used the camera exposure time will be approximately the same value as the length of the laser pulse. This technique can reduce background noise due to fluorescence.

Figure 2:
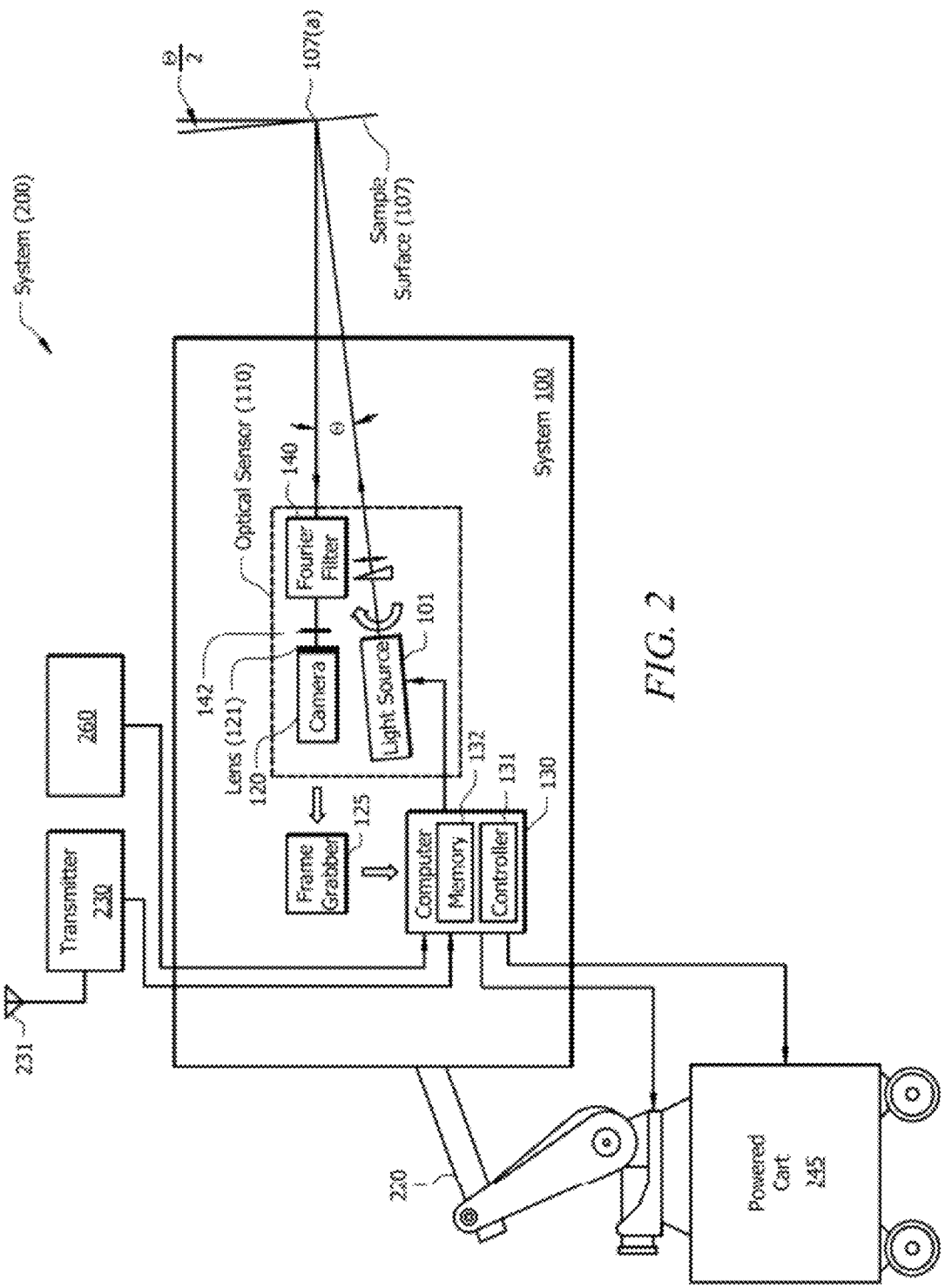
FIG. 2 is a depiction of an example automatic fingerprint scanning system comprising the example fingerprint system shown in FIG. 1A together with at least one scanner mechanically coupled to the optical sensor for scanning the optical sensor across a plurality of different surface portions within the region of interest, and a wireless transmitter for transmitting data representing fingerprints detected by the system to at least one remote site according to an example embodiment.

FIG. 2 is a depiction of an automatic fingerprint scanning system 200 comprising the example fingerprint system 100 shown in FIG. 1A together with at least one scanner 220 shown as a robotic arm 220 mechanically coupled to the system 100 for scanning the optical sensor 110 across a plurality of different surface portions within the region of interest, and a wireless transmitter 230 including an antenna 231 for transmitting data representing fingerprints detected by the system 100 to at least one remote site.

System 200 is shown also including a powered cart 245, such as a battery powered cart. Robotic arm 220 is affixed to the powered cart 245. System 200 also includes a remote sensing device 260 for generating a region image (e.g., 3D) across a region of interest, such as a room. The region image sensed by sensing device 260 is provided to computer or processor 130 and can be used to guide movements of the robot arm 220 for its movement to image across the region of interest, such as within a room.

Results can be stored in a local memory 132 associated with the computer or processor 130, and can be wirelessly transmitted by a wireless transmitter 230, such as in an established encoded protocol form, to one or more remote locations. In one embodiment the remote sensing device 260 comprises a Light Detection And Ranging (LIDAR) device. LIDAR may also be referred to as LADAR in military contexts, and is an optical remote sensing technology that can measure the distance to, or other properties of a target by illuminating the target with light, often using pulses from a laser Like the similar radar technology, which uses radio waves, the range to an object is determined by measuring the time delay between transmission of a pulse and detection of the reflected signal.

Figure 3A:
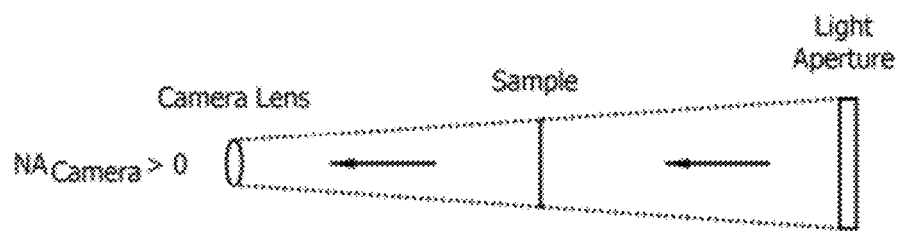
FIGS. 3A-C each depict different arrangements shown unfolded around the sample axis that can satisfy the condition that the entire sample surface be uniformly illuminated using equal and opposite light source and camera NAs, with the camera imaging the entire sample, according to example embodiments.
Figure 3B:
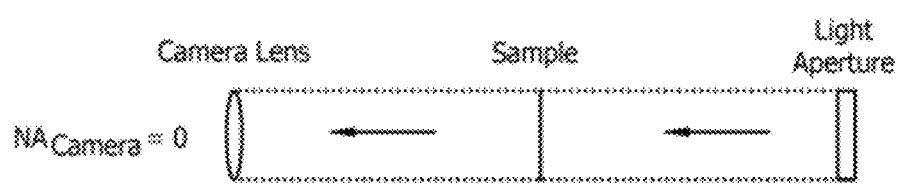
Figure 3C:
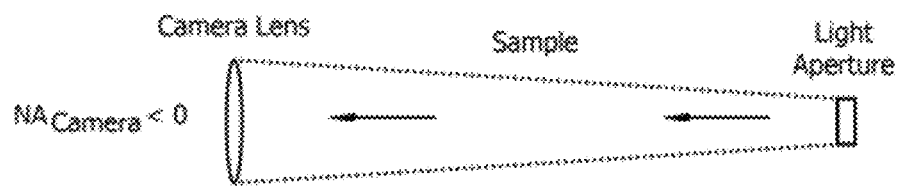

FIGS. 3A-C each depict different conditions shown unfolded around the sample axis that can satisfy the condition that the entire sample be uniformly illuminated using equal and opposite light source and $NA_{CAMERA}$, with the camera imaging the entire sample being irradiated, according to example embodiments. FIG. 3A shows the case of $NA_{CAMERA}>0$. Although the camera lens for $NA_{CAMERA}>0$ is realizable, there may be difficulty obtaining a light source the provides an equal and opposite NA. FIG. 3B shows the case of $NA_{CAMERA}=0$. In this case the camera lens can be a double telecentric lens. An example of a light source that provides a zero NA is a highly collimated light source. FIG. 3C shows the case of $NA_{CAMERA}<0$. Although obtaining a light source that provides an equal and opposite NA is reasonable, the camera lens for $NA_{CAMERA}<0$ may be difficult to realize.

Figure 4:
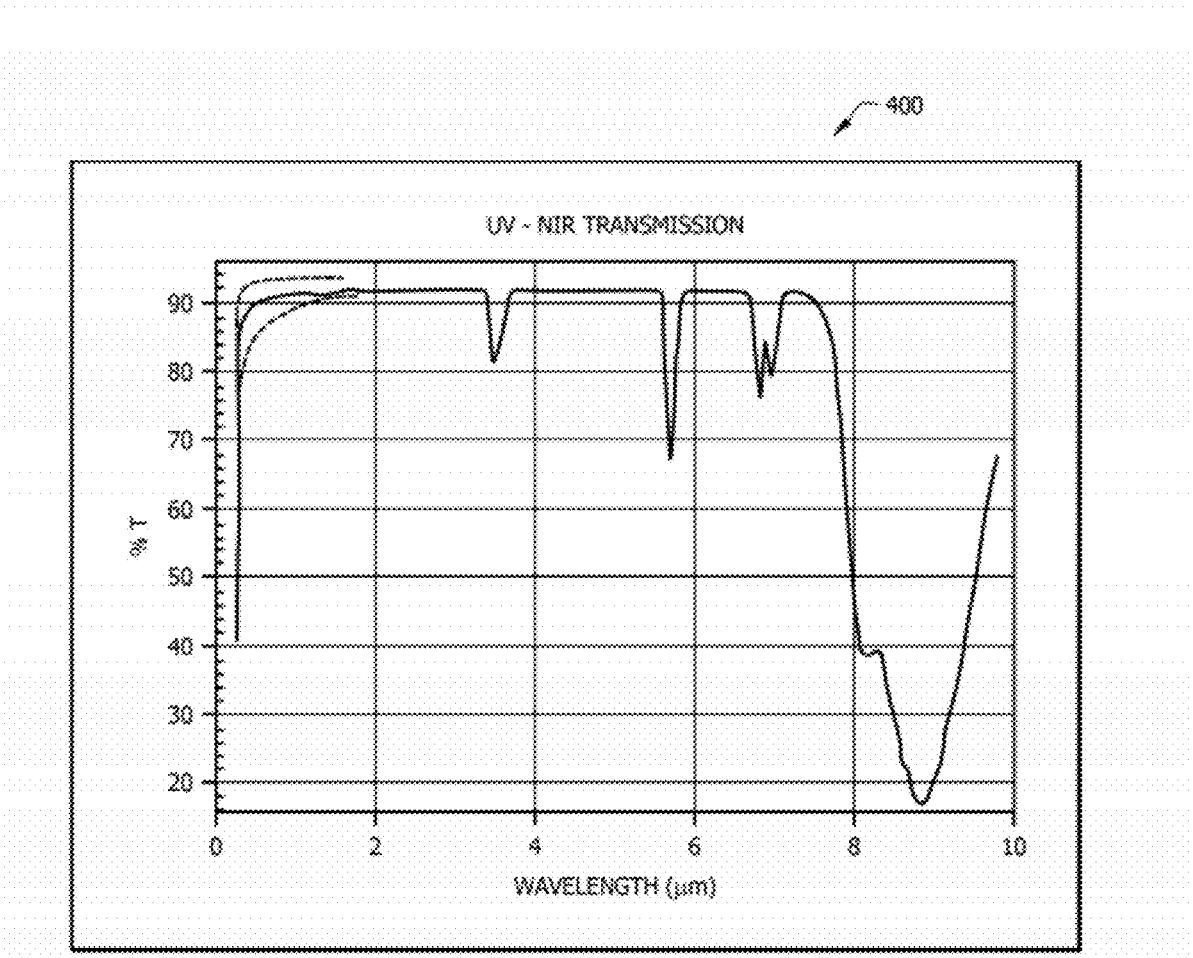
FIG. 4 is a plot transmission % from the UV to the Long Wave Infra-Red (LWIR) for fingerprint oil evidencing significantly enhanced absorption within the UV and the long wave infra red (LWIR) as compared to an absorption of fingerprint oil in a conventional wavelength range from visible light range to 3 μm. The UV and LWIR regions can be used to image fingerprints exploiting heightened body oil absorption that increases the optical contrast of the fingerprint oils against sample surfaces.

FIG. 4 is a plot 400 of UV to NIR transmission for fingerprint oil evidencing significantly enhanced absorption within the UV and the LWIR as compared to an absorption of fingerprint oil in a conventional visible light range (i.e. 500 nm) to 3 µm. The UV and LWIR can be used to image fingerprints exploiting heightened absorption to increase the optical contrast of the fingerprint oils against a sample surface, such as paper. In the UV, 80% transmission is at about 300 nm (0.3 µm), with the transmission decreasing (and absorption increasing due to oil absorption) to about 40% at 180 nm, with even lower transmission down to below 100 nm (not shown). Several IR absorption peaks are shown. Significantly enhanced absorption can thus be obtained at UV wavelength between 100 and 300 nm, and LWIR wavelengths at 3.42 µm, 5.71 µm, 6.9 µm, and 8.8 µm.

Figures 5A, 5B:
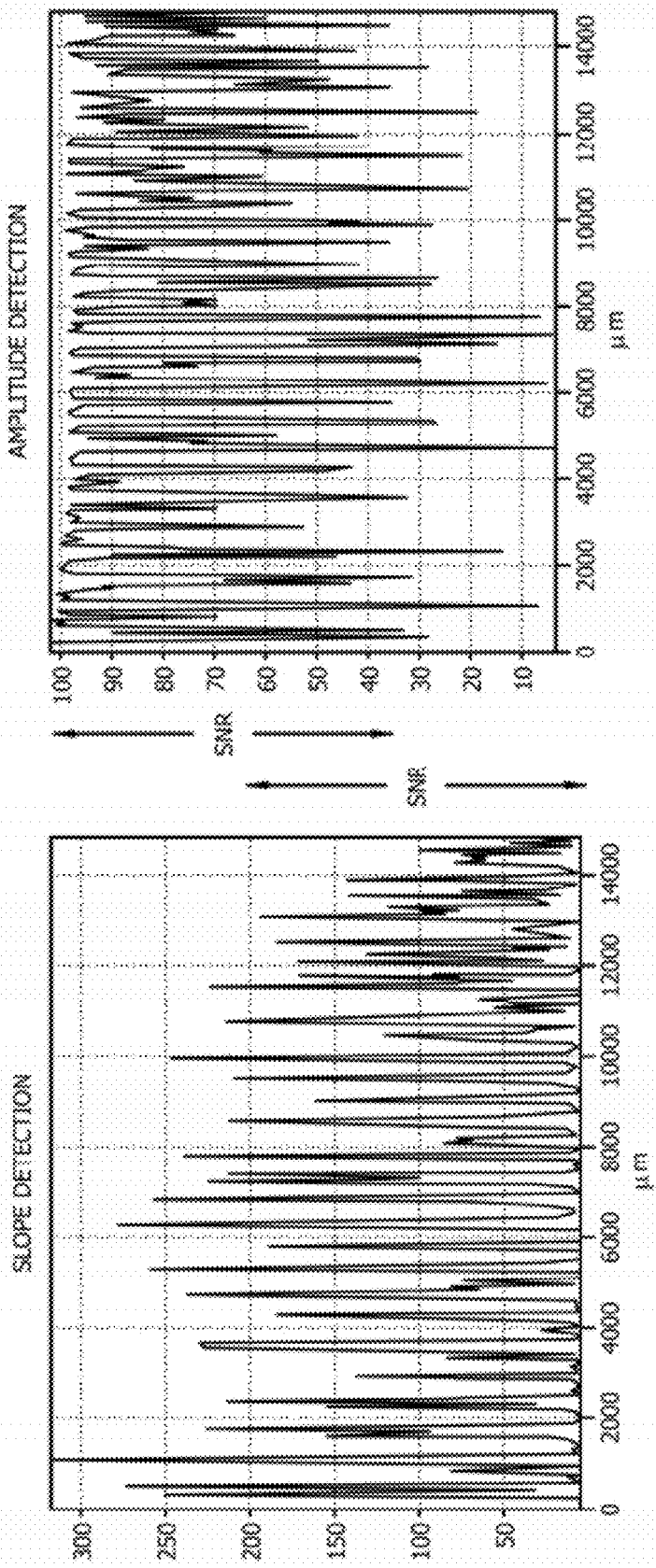
FIGS. 5A and B show signal to noise ratio (SNR) data from plots of fingerprint scans showing a ridge profile evidencing about a 3× improvement in SNR using slope detection (FIG. 5A) as compared to amplitude detection (FIG. 5B), according to an example embodiment.

FIGS. 5A and 5B show signal to noise ratio (SNR) data from plots of fingerprint scans showing a ridge profile evidencing about a 3× improvement in SNR using slope detection (FIG. 5A) as compared to amplitude detection (FIG. 5B), according to an example embodiment. The best possible detection would be an idealized "Matched Detection" where an exact replica of the feature being sought is compared with the collected signal. Amplitude Detection looks only for an amplitude change, while slope detection looks for a part of the feature being detected.

Figure 5C:
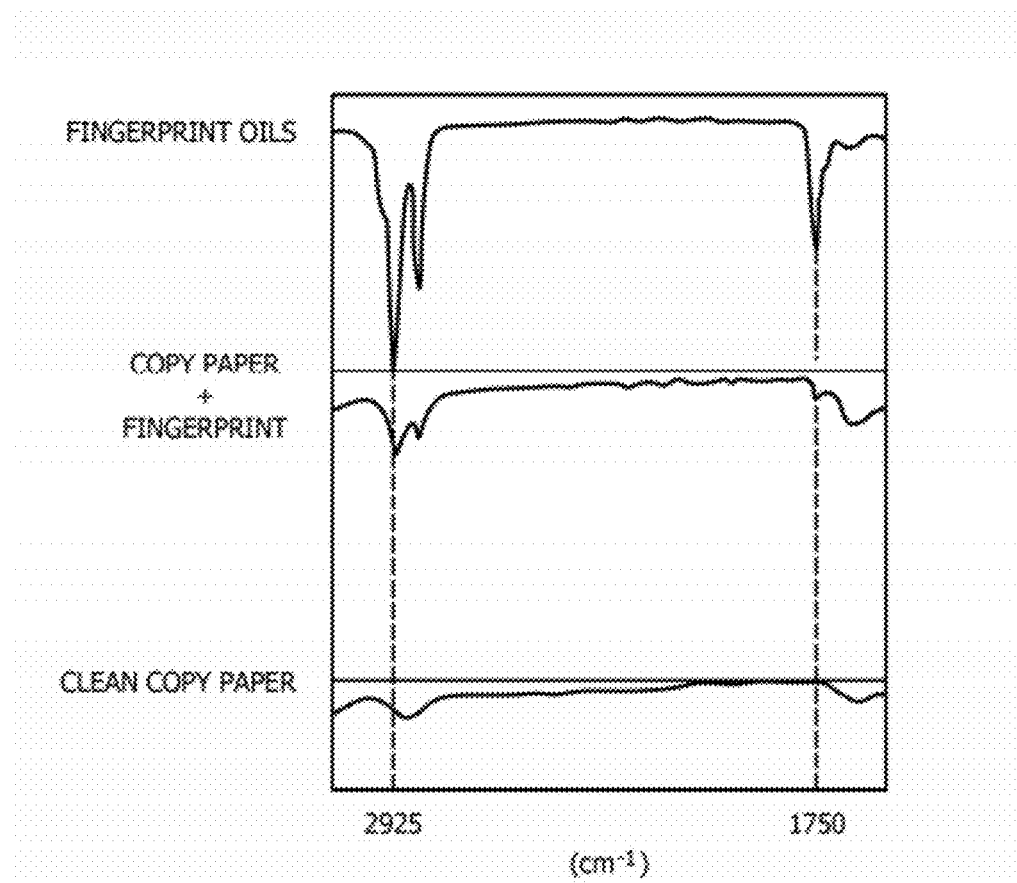
FIG. 5C provides spectral plots of the absorption for fingerprint oil, fingerprint oil on copy paper, and clean copy paper, showing an absorption peak at 2925 cm$^{-1}$ which corresponds to a wavelength of 3.418 μm that can be used to define sloped portions of this peak for slope detection, according to an example embodiment.

FIG. 5C is provides spectral plots of the absorption for fingerprint oil, fingerprint oil on copy paper, and clean copy paper, showing an absorption peak at 3.418 µm (2925 cm$^{-1}$ which corresponds to a wavelength of 3.418 µm) that can be used to define sloped portions of this peak for slope detection, according to an example embodiment. In the case of slope detection the feature being detected can be the sharp slopes on each side of the peak at 2925 cm$^{-1}$.

Figure 6:
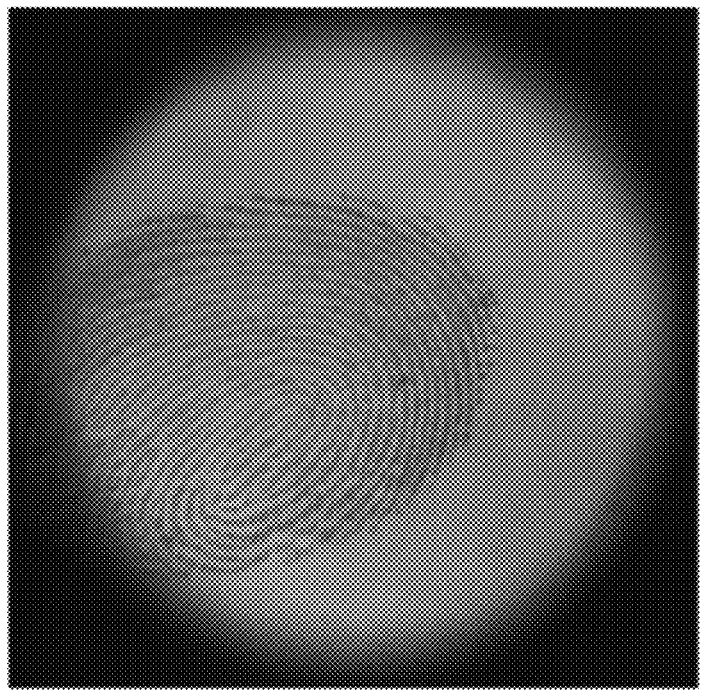
FIG. 6 is a scanned image of a fingerprint acquired by an example disclosed fingerprint system configured to be highly discriminating toward specular reflection from a sample surface including a critically aligned optical sensor having the light source and camera have equal and opposite NAs, according to an example embodiment.

FIG. 6 is a scanned image of a fingerprint acquired by an example disclosed fingerprint system configured to be highly discriminating toward specular reflection from a sample surface including a critically aligned optical sensor having the light source and camera have equal and opposite NAs, according to an example embodiment. The camera used was a 6M Pixel CCD, the lens was a double telecentric lens, and the light source was a set of fluorescent light bulbs held side-by-side closely to each other in a parallel fashion. The light source, sample and camera plus lens were set up to satisfy the critical angle condition.

Disclosed systems, such as systems 100, 160 and 200 described above, automatically generate fingerprint image data from sample surfaces within an interrogated region, and look for fingerprints in the fingerprint image data obtained. When a fingerprint is detected the system can capture the fingerprint, digitize it into a digital storage format (e.g., using an analog to digital converter), and can store it in memory, such as the internal memory 132 of computer 130. Computer 130 can comprise a laptop computer, personal digital assistants (PDAs) such as an IPHONE™, BLACKBERRY™, or other suitable portable computing device. Software on the portable computing device can then encode the stored fingerprints into a format usable by the existing AFIS (automated fingerprint identification system), integrated AFIS (IAFIS) or other fingerprint processing systems. In one application, disclosed systems can be used to help investigators locate latent fingerprints at a crime scene.

In one embodiment an internal matching algorithm helps the investigator(s) differentiate fingerprints of interest from those expected to see at the scene such as family members, co-workers, etc. Data from expected fingerprints can be loaded into the system and stored as reference fingerprint templates in local memory 132. Having the ability to immediately organize prints into classification groups can significantly benefit the investigators, helping them better focus their efforts.

Being automatic and computer controlled, disclosed embodiments reduce operator workload and minimize the potential for human error. Disclosed embodiments can also give the field investigator(s) the ability to immediately know that the data he/she gathers is valid and usable. Human error includes overlooking or possibly damaging critical evidence as well as incorrectly capturing fingerprint evidence. As described above, fingerprint data can be wireless transmitted to one or more remote locations using a wireless transmitter.

Disclosed fingerprint systems can be built into other systems to add security features to such systems, such as to reduce theft or unauthorized access. For example, credit or debit card processing systems can include disclosed fingerprint systems to provide a fingerprint record associated with each transaction that is triggered upon insertion of the card. Such fingerprint records can be used to identify the individual using the card, and if a fingerprint database is available, a fingerprint database can be used to determine whether account access will be provided.

While various disclosed embodiments have been described above, it should be understood that they have been presented by way of example only, and not as a limitation. Numerous changes to the disclosed embodiments can be made in accordance with the Disclosure herein without departing from the spirit or scope of this Disclosure. Thus, the breadth and scope of this Disclosure should not be limited by any of the above-described embodiments. Rather, the scope of this Disclosure should be defined in accordance with the following claims and their equivalents.

Although disclosed embodiments have been illustrated and described with respect to one or more implementations, equivalent alterations and modifications will occur to others skilled in the art upon the reading and understanding of this specification and the annexed drawings. While a particular feature may have been disclosed with respect to only one of several implementations, such a feature may be combined with one or more other features of the other implementations as may be desired and advantageous for any given or particular application.

The terminology used herein is for the purpose of describing particular embodiments only and is not intended to be limiting to this Disclosure. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

We claim:

1. An automatic fingerprint system, comprising:
an optical sensor, comprising:
a first light source that provides a collimated beam for interrogating sample surfaces including a first sample surface within a region of interest; and
a camera comprising a lens and a photodetector array optically coupled to said lens having a camera field of view ($FOV_{CAMERA}$), wherein said $FOV_{CAMERA}$ is large enough to image at least substantially an entire area of said first sample surface, and wherein said camera is critical angle positioned relative to said first light source to receive specular reflection (glare) from said first sample surface, wherein said camera generates image data from said glare;
wherein said first light source and said camera have substantially equal and opposite numerical apertures (NAs);
a computer or processor having associated memory that includes reference fingerprint templates coupled to receive a digitized form of said image data from said camera, wherein said computer or processor includes data processing software for (i) comparing said digitized form of said image data to said reference fingerprint templates to determine whether said image data includes at least one fingerprint and (ii) for generating a fingerprint image if said fingerprint is determined to be present.

2. The system of claim 1, wherein said first light source provides a uniformly extended collimated beam across a full area of said first sample surface.

3. The system of claim 1, wherein said NA of said camera=0, and wherein said lens comprises a double telecentric lens.

4. The system of claim 1, wherein said first light source comprises a broadband light source.

5. The system of claim 4, wherein said broadband light source comprises a plurality of fluorescent tubes aligned parallel to one another.

6. The system of claim 1, wherein said collimated beam comprises a narrowband beam.

7. The system of claim 6, wherein said first light source comprises a narrowband light source or a broadband light source including a spectrometer, and wherein said narrowband beam is at one or more ultraviolet (UV) wavelengths or one or more long wave infrared (LWIR) wavelengths that each corresponds to significantly enhanced absorption of fingerprint oil as compared to an absorption of said fingerprint oil in a visible light range.

8. The system of claim 7, wherein said at least one UV wavelength is between 100 and 300 nm, and wherein said LWIR wavelength is at 3.42 µm, 5.71 µm, 6.9 µm, or 8.8 µm.

9. The system of claim 1, wherein said generating said fingerprint image comprises slope detection.

10. The system of claim 1, further comprising at least one non-critically aligned light source for generating diffuse reflection from said first sample surface.

11. The system of claim 1, further comprising a local memory associated with said computer or processor for storing said fingerprint, and a wireless transmitter for transmitting data representing said fingerprint to at least one remote site.

12. The system of claim 11, wherein said computer or said processor and said wireless transmitter is provided by a portable computing device, said portable computing device utilizing said associated memory for storing said fingerprint, said associated memory including software for encoding said fingerprint into a predetermined format.

13. An automatic fingerprint scanning system, comprising:
an optical sensor, comprising:
a first light source that provides a collimated beam for interrogating sample surfaces including a first sample surface within a region of interest; and
a camera comprising a lens and a photodetector array optically coupled to said lens having a camera field of view ($FOV_{CAMERA}$), wherein said $FOV_{CAMERA}$ is large enough to image at least substantially an entire area of said first sample surface, and wherein said camera is critical angle positioned relative to said first light source to receive specular reflection (glare) from said first sample surface, wherein said camera generates image data from said glare;
wherein said first light source and said camera have substantially equal and opposite numerical apertures (NAs);
a computer or processor having associated memory that includes reference fingerprint templates coupled to receive a digitized form of said image data from said camera, wherein said computer or processor includes data processing software for (i) comparing said digitized form of said image data to said reference fingerprint templates to determine whether said image data includes at least one fingerprint and (ii) for generating a fingerprint image if said fingerprint is determined to be present, and
at least one scanner mechanically coupled to said optical sensor for scanning said optical sensor across a plurality of different surface portions within said region of interest,
wherein said critical angle positioning of said first light source to said FOV of said camera is maintained during said scanning.

14. The system of claim 13, wherein said NA of said camera=0, and wherein said lens comprises a double telecentric lens.

15. The system of claim 13, wherein said first light source comprises a broadband light source, and wherein said broadband light source comprises a plurality of fluorescent tubes aligned parallel to one another.

16. The system of claim 13, wherein said collimated beam comprises a narrowband beam, and wherein said collimated beam is at one or more ultraviolet (UV) wavelengths or one or more long wave infrared (LWIR) wavelengths that each corresponds to significantly enhanced absorption of fingerprint oil as compared to an absorption of said fingerprint oil in a visible light range.

17. The system of claim 16, wherein said at least one UV wavelength is between 100 and 300 nm, and wherein said LWIR wavelength is at 3.42 µm, 5.71 µm, 6.9 µm, or 8.8 µm.

18. The system of claim 13, wherein said generating said fingerprint image comprises slope detection.

19. The system of claim 13, further comprising at least one non-critically aligned light source for generating diffuse reflection from said first sample surface.

20. The system of claim 13, further comprising a local memory associated with said computer or processor for storing said fingerprint, and a wireless transmitter for transmitting data representing said fingerprint to at least one remote site.

21. The system of claim 20, wherein said computer or said processor and said wireless transmitter is provided by a portable computing device, said portable computing device utilizing said associated memory for storing said fingerprint, said associated memory including software for encoding said fingerprint into a predetermined format.

22. The system of claim 13, wherein said scanner comprises a robotic arm.

23. The system of claim 22, wherein said system further comprises a remote sensing device for generating a region image (3D) across said region of interest, wherein said region image is used by said robot arm for its movement to image across said region of interest.

24. The system of claim 23, wherein said remote sensing device comprises Light Detection And Ranging (LIDAR) device.

* * * * *